United States Patent [19]

Law et al.

[11] Patent Number: 5,130,443

[45] Date of Patent: Jul. 14, 1992

[54] PROCESS FOR THE PREPARATION OF ANILIDES

[75] Inventors: Kock-Yee Law, Penfield; Ihor W. Tarnawskyj, Rochester; F. Courtney Bailey, Webster, all of N.Y.

[73] Assignee: Xerox Corporation, Stamford, Conn.

[21] Appl. No.: 693,163

[22] Filed: Apr. 29, 1991

[51] Int. Cl.⁵ .......................................... C07D 209/86
[52] U.S. Cl. .................................................... 548/420
[58] Field of Search ......................................... 548/420

[56] References Cited

U.S. PATENT DOCUMENTS

| | | | |
|---|---|---|---|
| 4,382,934 | 5/1983 | Teraji et al. | 548/336 |
| 4,411,900 | 10/1983 | Ueda et al. | 548/203 |
| 4,797,337 | 1/1989 | Law et al. | 430/58 |
| 4,830,942 | 5/1989 | Fukagai et al. | 430/58 |
| 4,830,943 | 5/1989 | Sasaki et al. | 430/58 |
| 4,830,944 | 5/1989 | Umehara et al. | 430/59 |
| 4,833,052 | 5/1989 | Law et al. | 430/58 |
| 4,868,080 | 9/1989 | Umehara et al. | 430/73 |
| 4,916,039 | 4/1990 | Hashimoto et al. | 430/57 |
| 4,925,758 | 5/1990 | Hashimoto et al. | 430/57 |

FOREIGN PATENT DOCUMENTS 1258660 10/1989 Japan .

OTHER PUBLICATIONS

Hawley's Cond. Chem. Dict., 1987, p. 912 (Van Nostrand Reinhold).
March, Advanced Organic Chemistry 3rd ed, 1985, pp. 371-376.

Primary Examiner—Joseph Paul Brust
Assistant Examiner—M. S. H. Gabilan
Attorney, Agent, or Firm—E. O. Palazzo

[57] ABSTRACT

A process for the preparation of anilide couplers which comprises the reaction of an acid, an aromatic hydroxy compound, and an oxyhalide; isolating and purifying the aromatic ester formed; and subsequently reacting said ester with an aniline in the presence of a solvent.

18 Claims, 1 Drawing Sheet

| Anilide Product | % Yield | M.P. °C | IR (CM⁻¹) |
|---|---|---|---|
| (15) | 83% | >310 | 3,365 and 3,440 (N-H), 3,062 (aromatic C-H), 1,657 (amide C=O) |
| (16) | 89% | >310 | 3,358 and 3,430 (N-H), 3,062 (aromatic C-H), 1,658 (amide C=O) |
| (17) | 83% | 269.5 - 270.5 | 3,360 and 3,402 (N-H), 3,062 (aromatic C-H), 1,658 (amide C=O) |
| (18) | 78% | 311 - 312 | 3,322 and 3,375 (N-H), 3,062 (aromatic C-H), 1,652 (amide C=O) |
| (19) | 93% | >310 | 3,352 and 3,428 (N-H), 3,060 (aromatic C-H), 1,658 (amide C=O) |
| (20) | 90% | >310 | 3,368 and 3,416 (N-H), 3,062 (aromatic C-H), 1,660 (amide C=O) |
| (21) | 82% | >310 | 3,322, 3,360 and 3,428, (N-H), 3,060 (aromatic C-H), 1,660 (amide C=O) |
| (22) | 92% | 308 - 309 | 3,308, 3,412 and 3,440 (N-H), 1,650 (amide C=O) |
| (23) | 74% | 278 - 280 | 3,360 and 3,422 (N-H), 3,060 (aromatic C-H), 1,652 (amide C=O) |
| (24) | 73% | >310 | 3,306 and 3,448 (N-H), 1,660 (amide C=O) |
| (25) | 92% | >310 | 3,312 and 3,425 (N-H), 1,658 (amide C=O) |
| (26) | 78% | >310 | 3,302 and 3,448 (N-H), 3,065 (aromatic C-H), 1,656 (amide C=O) |
| (27) | 81% | >310 | 3,340 and 3,440 (N-H), 1,656 (amide C=O) |
| (28) | 73% | 278.5 - 279.5 | 3,328 and 3,430 (N-H), 3,065 (aromatic C-H), 1,654 (amide CO0) |
| (29) | 80% | >310 | 3,285 and 3,434 (N-H), 3,070 (aromatic C-H), 1,642 (amide C=O) |
| (30) | 91% | >310 | 3,320 (N-H), 1,663 (amide C=O) |

*FIG. 1*

PROCESS FOR THE PREPARATION OF ANILIDES

BACKGROUND OF THE INVENTION

This invention is generally directed to processes for the preparation of anilides, and more specifically anilide couplers which can be selected for the preparation of photogenerating azo compositions, such as bisazos and trisazos. In one embodiment of the present invention, there are provided simple, economical processes for the preparation of photoreceptor grade anilide couplers, such as 2-hydroxy-11H-benzo(a)carbozole-3-carboxanilide and its derivatives, by the reaction of an aromatic, especially phenyl ester obtained from an acid with an aniline. One process embodiment of the present invention comprises the reaction of a hydroxybenzocarbazole carboxylic acid with phenol, followed by the reaction of the resulting carboxylate with an aniline. The couplers resulting with the processes of the present invention can be selected for the preparation of azo photogenerating pigments, reference for example U.S. Pat. No. 4,916,039, and 4,925,758, the disclosures of which are totally incorporated herein by reference. The aforementioned photogenerating pigments can be selected for layered photoresponsive imaging members comprised of a charge transport layer, a photogenerating layer and a supporting substrate. More specifically, the azo photogenerating pigments that can be obtained with the processes of the present invention can be selected for layered photoconductive imaging members with improved xerographic properties, inclusive of high charge acceptance, low dark decay, high photosensitivity, including photosensitivity in the wavelength regions of from about 400 to about 850 nanometers, enabling their selection for electrophotographic, especially xerographic imaging systems, LED printers, and diode laser printers which are usually sensitive to wavelengths of from about 660 to about 800 nanometers. The imaging members can be comprised of photoconductive layers comprised of the bisazo pigments and charge or hole transport layers, especially those comprised of aryl amines, which members can be sensitive to light in the wavelength region of from about 400 to about 800 nanometers. The resulting members are responsive to visible light, and near infrared illumination originating from laser printing apparatuses wherein, for example, gallium arsenide diode lasers are selected. The photoresponsive imaging members can also, for example, contain situated between a photogenerating layer and a hole transporting layer, or situated between a photogenerating layer and a supporting substrate with a charge transport layer in contact with the photogenerating layer, a photoconductive composition comprised of the photogenerating azo pigments.

Examples of advantages associated with the processes of the present invention include obtaining couplers with high purity, for example from about 95 to about 99 percent or higher in embodiments; immediate utilization of the couplers obtained for the preparation of bisazo photogenerating pigments; acceptable yields of, for example, from about 55 to about 95 percent; the product can be easily purified by conventional techniques such as solvent extraction, recrystallization and the like; scale up to manufacturing conditions is enabled in embodiments thereof; the products obtained can be, after synthesis, selected for the preparation of photogenerating azo pigments, and wherein the resulting xerographic properties of the photoconductive members such as dark decay, charge acceptance, and charge stability are acceptable; and the like.

The preparation by certain methods of anilide couplers are known. More specifically, there is disclosed in Japanese Laid Open 59-137459, 1984, the preparation of 2-hydroxy-11H-benzo(a)carbazole-3-carbohydrozide by initially preparing a methyl ester (methyl 2-hydroxy-11H-benzo(a)carbazole-3-carboxylate) and condensing this ester with a hydrazine. Also, in the Color Index, Third Edition, Volume 4, published by the Society of Dyes and Colorants, there is illustrated the preparation of methoxy anilides, such as 2-hydroxy-11H-benzo(a)-carbazole-3-carbox-2'-methyl-4'-methoxyanilide, by the condensation of an acid with an appropriate aniline. Other representative prior art disclosing the preparation of couplers include U.S. Pat. Nos. 4,916,039 and 4,925,758 wherein there is illustrated the conversion of an appropriate acid to an acid halide such as acid chloride, and subsequently reacting the resulting acid halide with an aniline to obtain an anilide coupler.

Also, many processes are known for the preparation of azo photogenerating pigments, such as azotization and coupling, reference U.S. Pat. No. 3,898,084. Examples of aromatic amines selected for the preparation of azo pigments include 2,7-diaminofluorenone, reference for example, U.S. Pat. Nos. 4,797,337; 4,830,942; 4,822,705; 4,596,754; 4,618,672; 4,481,271; 4,400,455; 4,390,608; 4,327,176; 4,314,015; 4,299,015; 4,299,896 and 4,551,404 possess in many instances high sensitivity and high electrical stability. Azo pigments synthesized from anilide couplers of 2-hydroxy-11H-benzo(a)carbazole-3-carboxylic acid enable imaging members with photoresponses at longer wavelengths, for example beyond 700 nanometers.

In U.S. Pat. No. 4,916,039 there are disclosed photoconductors with charge generating pigments comprised of certain azo compounds, reference the formula illustrated in the Abstract of the Disclosure, and in column 3. The aforementioned azo pigments are prepared by the coupling reaction of 2-hydroxy-3-carbamoylbenzo-alpha-carbazole derivatives of Formula VI with diazonium salts, reference columns 6 and 7. The coupling reaction is accomplished by dissolving the diazonium salts and a coupler, such as those obtained with the processes of the present invention in an organic solvent, such as DMF and DMSO and adding dropwise thereto an alkaline aqueous solution at a temperature of from about −10° to about 40° C., see column 7 for example. A similar teaching is present in U.S. Pat. No. 4,925,758.

Imaging members with certain bisazo pigments are known, reference for example U.S. Pat. No. 3,898,084, which discloses, for example, the azo pigment chlorodiane blue in a photoconductive imaging member. The aforementioned chlorodiane blue can be prepared by azotizing dichlorobenzidine in HCl, for example 18 percent HCl, by the addition of a sodium nitrite, followed by the addition of HBF$_4$, enabling the formation of the tetrazonium salt. This salt can then be coupled with 2-hydroxy-3-naphthanilide to permit the formation of the chlorodiane blue pigment, which formation is accomplished in the presence of sodium acetate.

U.S. Pat. No. 3,574,181 discloses disazo compounds useful as coloring agents. Composite electrophotographic photosensitive materials containing various azo compounds are disclosed in U.S. Pat. No. 4,618,672, wherein bisazo compounds particularly suitable for use in the charge generating layer of a layered electrophotographic photoconductor are illustrated. Similarly, an article by M. Hashimoto entitled "Electrophotographic Sensitivity of Fluorenone Bisazo Pigments", Electrophotography, Vol. 25, No. 3 (1986), discloses disazo compounds as charge generating materials in electrophotographic layered photoreceptors. Further, Japanese Patent Kokai No. 54-20736 discloses disazo pigments as constituents in electrophotographic processes. Japanese Patent 58-177955 also discloses many disazo compounds suitable for use in the photosensitive layer of an electrophotographic device.

U.S. Pat. No. 4,713,307, the disclosure of which is hereby totally incorporated by reference, discloses photoconductive imaging members containing a supporting substrate, certain azo pigments as photogenerating materials, and a hole transport layer that preferably contains an aryl diamine compound dispersed in an inactive resinous binder. The aforementioned azo pigments can be obtained from the couplers generated with the processes of the present invention.

U.S. Pat. No. 4,797,337, the disclosure of which is totally incorporated herein by reference, discloses a photoconductive imaging member comprising a supporting substrate, a hole transport layer, and a photogenerating layer comprising specific disazo compounds, which disazo compounds are prepared as illustrated herein, that is by the azotization and coupling reactions illustrated in the aforementioned prior art.

Additional references illustrating layered organic electrophotographic photoconductor elements with azo, bisazo, related compounds, and processes thereof include U.S. Pat. No. 4,390,611, U.S. Pat. No. 4,551,404, U.S. Pat. No. 4,596,754, Japanese Patent 60-64354, U.S. Pat. No. 4,400,455, U.S. Pat. No. 4,390,608, U.S. Pat. No. 4,327,168, U.S. Pat. No. 4,299,896, U.S. Pat. No. 4,314,015, U.S. Pat. No. 4,486,522, U.S. Pat. No. 4,486,519, U.S. Pat. No. 4,555,667, U.S. Pat. No. 4,440,845, U.S. Pat. No. 4,486,800, U.S. Pat. No. 4,309,611, U.S. Pat. No. 4,418,133, U.S. Pat. No. 4,293,628, U.S. Pat. No. 4,427,753, U.S. Pat. No. 4,495,264, U.S. Pat. No. 4,359,513, U.S. Pat. No. 3,898,084, U.S. Pat. No. 4,830,944, U.S. Pat. No. 4,820,602, and Japanese Patent Publication 60-111247.

In U.S. Pat. No. 4,833,052, the disclosure of which is totally incorporated herein by reference, there are illustrated certain bisazo photoconductive imaging members. Examples of bisazo compounds disclosed in this patent include those of the formulas as illustrated in column 4, such as 4,4'-bis(1"-azo-2"-hydroxy-3"-naphthanilide)-1,1'-dianthraquinonylamine.

In a patentability search report the following United States patents were recited: U.S. Pat. No. 4,830,943 relating to a photoconductor with a disazo having couplers, such as anilides, carbozole, and the like; U.S. Pat. No. 4,833,052 which discloses a photoconductive imaging member comprising a disazo compound with an azoic coupler, such as an anilide and the like, note column 7, lines 44 to 58; U.S. Pat. No. 4,868,880 which discloses a photosensitive layer comprising an azo pigment having an organic residue, see column 2, lines 53 to 65; and U.S. Pat. No. 4,830,944 which discloses a charge generation material comprising a disazo pigment with couplers, such as those derived from carboxylic acids.

SUMMARY OF THE INVENTION

It is a feature of the present invention to provide processes for the preparation of anilide couplers that can be selected for the generation of azo photogenerating pigments.

Another feature of the present invention is to provide economical, efficient processes for the preparation of anilide couplers that can be selected for the generation of azo photogenerating pigments.

Another feature of the present invention is to provide processes for the preparation of substantially pure anilide couplers that can be selected for the generation of azo, especially bisazo, photogenerating pigments.

In another feature of the present invention there are provided processes for the preparation of substantially pure couplers in acceptable yields that can be selected for the generation of azo, especially bisazo, photogenerating pigments.

Another feature of the present invention is to provide processes for the preparation of bisazo, photogenerating pigments, and imaging members thereof, which members can be sensitive to wavelengths of from about 400 to about 850 and preferably from about 400 to about 800 nanometers.

Another feature of the present invention resides in the provision of azo, especially bisazo, photoresponsive imaging members which can possess excellent dark decay properties, high charge acceptance values, and electrical stability.

Further, in another feature of the present invention there are provided photoconductive imaging members that can be simultaneously responsive to infrared light, and to visible light.

Additionally, another feature of the present invention resides in the provision of imaging and printing methods with the photoconductive imaging members illustrated herein.

These and other features of the present invention in embodiments thereof can be accomplished by the provision of processes for the preparation of couplers, azo, especially bisazo, compounds thereof, and imaging members thereof. More specifically, the present invention is directed to processes for the preparation of the anilide couplers of 2-hydroxy-11H-benzo(a)carbazole-3-carboxylic acid derivatives such as 2-hydroxy-8-chloro-11H-benzo(a)carbazole-3-carboxylic acid, 2-hydroxy-8-fluoro-11H-benzo(a)carbazole-3-carboxylic acid, and the like by the reaction of the corresponding carboxylate with an aniline. The azo, especially bisazo, photogenerating pigments can then be prepared by coupling the azonium salt of an aromatic amine with the anilide couplers of 2-hydroxy-11H-benzo(a)carbozole-3-carboxylic acid.

Embodiments of the present invention include a process for the preparation of anilide couplers which comprises the reaction of an acid, an aromatic hydroxy compound, and an oxyhalide; isolating and purifying the aromatic ester formed; and subsequently reacting the formed ester with an aniline in the presence of a solvent; and a process which comprises the reaction in an aromatic hydrocarbon solvent of 2-hydroxy-11H-benzo(a)carbazole-3-carboxylic acid, or similar acid with a phenol, or substituted phenol, and a phosphorus oxyhalide; isolating and purifying the resulting aromatic ester; and subsequently reacting the ester with an aniline in the presence of a polar solvent.

DESCRIPTION OF FIGURE

Illustrated in FIG. 1, is a table providing information and data relating to the preparation of the anilide couplers indicated.

In one specific embodiment, the process of the present invention comprises the reaction of 2-hydroxy-11H-benzo(a)carbazole-3-carboxylic acid, with an aromatic hydroxy compound, such as a substituted phenol, in an aromatic hydrocarbon solvent. The aforementioned mixture can be heated at a temperature of, for example, from about 80° to about 200° C. Subsequently, there is added to the reaction mixture an oxyhalide, such as phosphorus oxychloride, followed by the addition of an aliphatic alcohol, such as methanol, resulting in a solid product of, for example, phenyl 2-hydroxy-11H-benzo(a)carbazole-3-carboxylate after separation by, for example, filtration. The aformentioned obtained carboxylate or a phenyl ester can then be reacted with aniline in a solvent, such as N-methyl pyrrolidinone with heating. The precipitated coupler product, such as 2-hydroxy-11H-benzo(a)carbazole-3-carboxanilide, resulting can be isolated by a number of known methods, such as filtration, and optionally, but preferably washed with solvents and water. Similar couplers, such as 2-hydroxy-11H-benzo(a)carbazole-3-carbox-o-ethylanilide, 2-hydroxy-11H-benzo(a)carbazole-3-carbox-p-chloroanilide, 2-hydroxy-11H-benzo(a)carbazole-3-carbox-p-methylanilide, and the like, can be prepared by selecting as a reactant a substituted aniline, such as an alkyl aniline with, for example, from about 1 to about 20 carbon atoms, such as ethyl aniline; haloanilines, such as chloro anilines; and the like. There results anilide couplers in high purity, for example better than 95 percent, such as 2-hydroxy-11H-benzo(a)carbazole-3-carboxanilde, which couplers can be selected for the preparation of azo photogenerating pigments by known processes as illustrated, for example, in a number of the U.S. patents mentioned herein.

The process of the present invention is further illustrated with reference to the following general and specific reaction schemes wherein in the general reaction scheme X is a substituent such as hydrogen, halogen including chlorine, fluorine or bromine, alkyl with from 1 to about 10 carbon atoms such as methyl, ethyl, propyl, butyl, pentyl and the like; alkoxy containing, for example, from 1 to about 10 carbon atoms such as methoxy, propoxy, butoxy, pentoxy and the like; and other substituents; n is a number of, for example, 0, 1, 2, 3 or 4, and Ar and Ar' are aromatic or substituted aromatic groups such as phenyl and naphthyl, which components can have present thereon various substituents such as alkyl, alkoxy, and the like. Known aromatic solvents can be selected, such as benzene, xylene, and the like, which solvents are utilized in effective amounts.

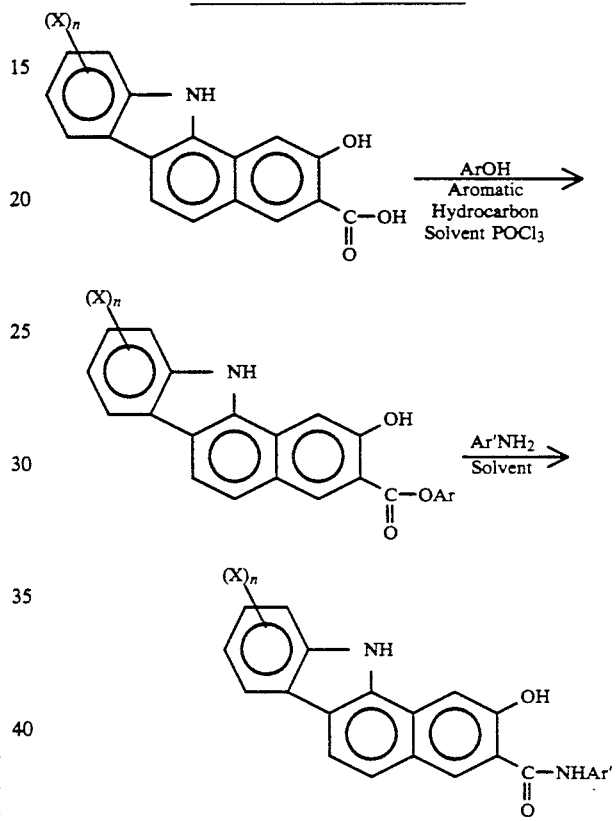

GENERAL REACTION - I

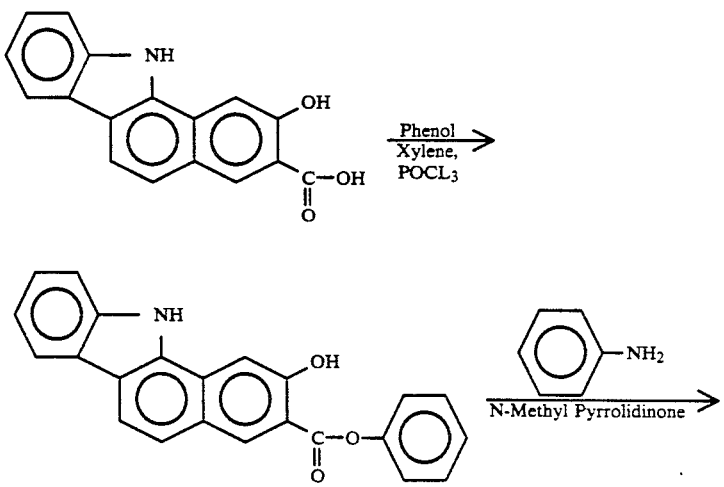

SPECIFIC REACTION - II

SPECIFIC REACTION - II

-continued

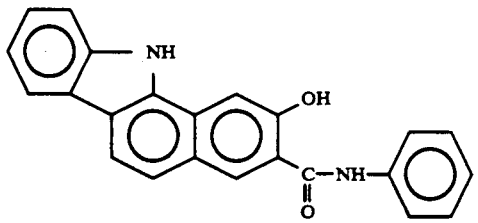

The anilide couplers can be prepared in an embodiment by first converting the carboxylic acid to an aromatic ester and then reacting the aromatic ester with an aniline in a solvent. More specifically, the aromatic ester can be prepared by reacting a hydroxybenzo(a)-carbazole-3-carboxylic acid, such as 2-hydroxy-11H-benzo(a)carbazole-3-carboxylic acid with an aromatic hydroxy compound such as phenol, p-chlorophenol, and the like in an aromatic solvent such as xylene or chlorobenzene. The esterification reaction can be facilitated by adding to the reaction mixture an oxyhalide, such as phosphorous oxychloride. The ratio of the acid to the hydroxy compound can be, for example, 1 to 1 depending on the reactivity of the acid and the reaction temperature. Optionally, phenol can be used as a solvent for the reaction. The reaction can be accomplished at effective temperatures of, for example, from about 80° C. to about 200° C. After the consumption of the starting acid, an alcohol such as methanol can be added and the precipitated product, the aromatic ester, such as phenyl 2-hydroxy-11H-benzo(a)carbazole-3-carboxylate, is isolated by filtration. The aromatic ester can then be purified by conventional techniques, such as solvent extraction or recrystallization. The resulting product is usually pure, namely a single component is evidenced in chromatographic analyses, and is characterized by melting point, infrared spectroscopy, mass spectrometry, NMR spectroscopy, especially $^{13}C$ NMR spectroscopy as well as elemental analysis.

The aromatic ester is reacted with an aniline in a solvent and heating to form the anilide product. The reaction temperature can be varied to from about 140° C. to about 280° C. or above. Specifically, phenyl 2-hydroxy-11H-benzo(a)carbazole-3-carboxylate can be reacted with aniline in methyl N-pyrrolidinone at about 250° C. The ratio of the phenyl ester to aniline can vary, for example, from about 1:1 equivalent and up to about 20 equivalents. After the reaction is completed, the product mixture is cooled to room temperature, about 25° C., and discharged into an acidic aqueous solution, such as a 5 percent HCl ice cold solution. The precipitated anilide product, such as 2-hydroxy-11H-benzo(a)-carbazole-3-carboxanilide, is isolated by filtration and washed with water and methanol. Purification can be accomplished by first dissolving the crude product in a hot solvent, such as DMF, and then precipitating the product by adding water or methanol, or a mixture of methanol and water. The purified product is then characterized by melting point, IR, mass spectrometry, NMR spectroscopy, especially $^{13}C$ NMR as well as elemental analysis.

In an embodiment, the present invention comprises the first reaction of a carboxylic acid and a phenol in an aromatic solvent, which reaction is accomplished in the presence of an oxyhalide. Carboxylic acid examples include, for example, 2-hydroxy-11H-benzo(a)carbazole-3-carboxylic acid, 2-hydroxy-8-chloro-11H-benzo(a)carbazole-3-carboxylic acid, 2-hydroxy-8-fluoro-11H-benzo(a)carbazole-3-carboxylic acid, and the like including other similar known acids. Various known phenol reactants can be selected such as halophenols, like chlorophenol, fluorophenol, alkyl phenols, especially wherein alkyl includes from 1 to about 18 carbon atoms such as methylphenol, ethylphenol, propylphenol, butylphenol, heptylphenol, hexylphenol, and the like; or a naphthol, such as 1-naphthol, 2-naphthol, an alkoxyphenol, wherein alkoxy contains, for example, from 1 to about 18 carbon atoms, such as methoxyphenol, ethoxyphenol, propoxyphenol, butoxyphenol, and the like. A number of known aromatic solvents may be selected such as benzene, toluene, xylene, halobenzene, especially chlorobenzene, and the like. Typical reaction temperatures are from about 80 to about 200, and preferably from about 100° to about 180° C. Numerous known oxyhalides can be selected, such as phosphorous oxychloride, and the like. Various effective amounts of reactants can be utilized, thus for example the ratio of acid to phenol can be 1:1, up to reacting the acid in a pure phenol with from about 2 to about 8 equivalents of the phenol relative to the acid being selected. Typical solvent amounts include from zero to about 200 milliliters, and preferably from about 50 to 100 milliliters per about 10 grams of acid. The aromatic ester formed is usually isolated by known means such as filtration and can then be purified by solvent washing or other conventional techniques such as recrystallization or extraction. Thereafter, a second reaction is accomplished wherein the aforementioned purified ester is reacted with an aniline in a solvent to form the desired anilide coupler product. Typical amounts of esters and anilines selected can be, for example, from a 1:1 ratio, 1 to 25, or from about 2 to about 20 ester to aniline parts being selected. Various suitable known solvents can be selected such as N,N-dimethylformamide, N,N-dimethylacetamide, N-methyl pyrrolidinone, and the like. About 5 milliliters to 100 milliliters of solvent for each 5 grams of ester reactant with from about 10 to 50 milliliters of solvent can normally be selected for example. A number of suitable reaction temperatures can be selected, including for example from about 140 to about 280, and preferably from about 180° to about 260° C. Numerous ester reactants can be utilized as illustrated herein, such as phenyl 2-hydroxy-11H-benzo(a)carbazole-3-carboxylate, phenyl 2-hydroxy-8-fluoro-11H-benzo(a)carbazole-3-carboxylate, and the like. Known anilines can be selected, such as alkylanilines like methylaniline, alkoxyanilines like methoxyaniline, haloanilines like chloroaniline, trifluoromethanilines, nitroanilines, naphthylamines, and the like.

The anilide products synthesized and purified as illustrated herein can be selected for the preparation of photogenerating azo components, such as those illustrated in U.S. Pat. Nos. 4,916,039 and 4,925,758, the disclosures of which are totally incorporated herein by reference, usually exhibit a single component in chromatographic analysis. No impure signal can be observed in the $^{13}$C NMR spectra. The resulting anilide products can then be selected directly for the synthesis of various photogenerating azo pigments by known azotization coupling processes as illustrated, for example, in a number of the U.S. patents mentioned herein.

These photogenerating azos can be incorporated into various photoconductive imaging members. One such member is comprised of a supporting substrate, a hole transport layer, and as a photoconductive layer situated between the supporting substrate, and the hole transport layer the azo compounds. In another embodiment, there is envisioned a layered photoresponsive device comprised of a supporting substrate, a photoconductive layer comprised of the azo compounds obtained with the processes of the present invention; and situated between the supporting substrate and the photoconductive layer, a charge transport layer. In one specific illustrative embodiment, the photoresponsive device can be comprised of (1) a supporting substrate; (2) a hole blocking layer; (3) an optional adhesive interface layer; (4) a photogenerating layer comprised of the azo pigments obtained with the processes of the present invention; and (5) a charge, especially hole transport layer. Thus, a specific photoresponsive device of the present invention can be comprised of a conductive supporting substrate, a hole blocking metal oxide layer in contact therewith, an adhesive layer, the azo compound photogenerating material overcoated on the optional adhesive layer, and as a top layer, a hole transport layer comprised of certain diamines dispersed in a resinous matrix. The photoconductive layer composition, when in contact with the hole transport layer, is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference. Also, examples of charge transport molecules are illustrated in U.S. Pat. No. 4,921,773, and the patents mentioned therein, the disclosures of each of the aforementioned patents, including the '773 patent, being totally incorporated herein by reference.

The photoresponsive devices described herein can be incorporated into various imaging systems such as those conventionally known as xerographic imaging processes. Additionally, the imaging members can be selected for imaging and printing systems with visible light and/or infrared light. In this embodiment, the photoresponsive devices may be negatively charged, exposed to light in a wavelength of from about 400 to about 850, and preferably from about 400 to about 800 nanometers, either sequentially or simultaneously, followed by developing the resulting image and transferring to paper.

The supporting substrate for the imaging members may comprise an insulating material such as an inorganic or organic polymeric material, including MYLAR ®, a commercially available polymer; a layer of an organic or inorganic material having a semiconductive surface layer such as indium tin oxide or aluminum arranged thereon; or a conductive material such as aluminum, titanium, chromium, nickel, brass, or the like. The substrate may be flexible, seamless, or rigid and may have a number of different configurations, such as a plate, a cylindrical drum, a scroll, an endless flexible belt, and the like. In one embodiment, the substrate is in the form of an endless flexible belt. In some situations, it may be desirable to coat an anticurl layer, such as polycarbonate materials commercially available as MAKROLON ®, on the back of the substrate, particularly when the substrate is an organic polymeric material.

The thickness of the substrate layer depends on a number of factors, including economic considerations, the components of the other layers, and the like. Thus, this layer may be of substantial thickness, for example up to 125 mils, or of minimal thickness provided that there are no adverse effects on the system. In embodiments, the thickness of this layer is from about 3 mils to about 20 mils.

Generally, the azo photogenerating layer has a thickness of from about 0.05 micron to about 10 microns or more, and preferably has a thickness of from about 0.1 micron to about 4 microns. The thickness of this layer, however, is dependent primarily upon the photogenerating weight loading, which may vary from about 5 to 100 percent, the components of the other layers, and the like. Generally, it is desirable to provide this layer in a thickness sufficient to absorb a substantial amount, for example from about 80 to about 90 percent or more, of the incident radiation which is directed upon it in the imagewise or printing exposure step. The maximum thickness of this layer is dependent primarily upon factors such as mechanical considerations, such as the specific azo compound selected, the thickness of the other layers, and whether a flexible photoconductive imaging member is desired. Optionally, resin binders for the photogeneration layer include poly(vinyl acetal) such as polyvinyl formal, and the like.

The charge transport layer can be comprised of various components providing, for example, that they effectively transport charges (holes) such as an aryl amine compound dispersed in a resinous binder and other components, reference the '773 patent mentioned herein, the disclosure of which is totally incorporated herein by reference. In one embodiment, the known hole transport layers are comprised of aryl amine compounds of the formula:

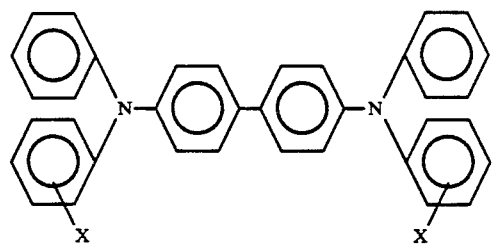

wherein X is selected from the group consisting of alkyl and halogen. Preferably, X is selected from the group consisting of methyl and chloride in either the ortho, meta, or para position. Suitable inactive binder materials for the hole transport layer include known highly insulating resins, which generally have a resistivity of at least $10^{12}$ ohm-cm to prevent undue dark decay. Compounds corresponding to the above formula include N,N-diphenyl-N,N'-bis(alkylphenyl)-[1,1'-biphenyl]-4,4'-diamine, wherein alkyl is selected from the group consisting of methyl, such as 2-methyl, 3-methyl and 4-methyl, ethyl, propyl, butyl, hexyl, and the like. With halo substitution, the amine is N,N'-diphenyl-N,N'-bis(halo phenyl)-[1,1'-biphenyl]-4,4'-diamine, wherein halo is 2-chloro, 3-chloro or 4-chloro. Other electrically active small molecules that can be dispersed in the electrically inactive resin to form a layer which will transport holes include bis(4-diethylamino-2-methylphenyl)phenyl methane, 4',4''-bis(diethylamino)-2',2''-dimethyltriphenyl methane, bis-4-(diethylaminophenyl)phenyl methane, and 4,4'-bis(diethylamino)-2,2'-dimethyltriphenyl methane. Generally, the hole transport layer has a thickness of from about 5 to about 75 microns, and preferably of from about 10 to about 40 microns.

Examples of highly insulating and transparent resinous components or inactive binder resinous material for the transport layer include materials such as those described in U.S. Pat. No. 3,121,006, the disclosure of which is totally incorporated herein by reference. Specific examples of suitable organic resinous materials include polycarbonates, arcylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. The materials most preferred as electrically inactive resinous materials in embodiments of the present invention are poly(4,4'-dipropylidinediphenyline carbonate) with a weight average molecular weight of from about 35,000 to about 40,000 available as LEXAN 145 TM from General Electric Company; poly(4,4'-isopropylidine-diphenyline carbonate) with a weight average molecular weight of from about 40,000 to about 45,000 available as LEXAN 141 TM from General Electric Company; a polycarbonate resin having a weight average molecular weight of from about 50,000 to about 100,000, available as MAKROLON TM from Farbenfabricken Bayer AG; and a polycarbonate having a weight average molecular weight of from about 20,000 to about 50,000, available as MERLON TM from Mobay Chemical Company. Generally, the resinous binder contains from about 10 to about 75 percent by weight of the active material corresponding to the foregoing formula, and preferably from about 35 percent to about 50 percent of this material. Examples of binder material for the azo photogenerating layer are poly(vinyl acetals), polycarbonates as mentioned herein, polyesters, polyvinyl carbazole, and the like. Typical effective amounts of binder can be selected including, for example, from about 5 to about 95, and preferably from about 10 to about 70 weight percent, in embodiments of the present invention.

The photoconductive imaging member may optionally contain a hole blocking layer situated between the supporting substrate and the photogenerating layer. This layer may comprise metal oxides, such as aluminum oxide and the like, or materials such as silanes. The primary purpose of this layer is to prevent hole injection from the substrate during and after charging. Typically, this layer is of a thickness of about 5 to about 300 Angstroms, although it may be as thick as 500 Angstroms in some instances.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is, for example, of a thickness of less than about 0.6 micron, with a thickness range of from about 0.05 to about 1 micron being suitable in embodiments of the present invention.

The imaging members with the azos illustrated herein can permit excellent xerographic properties in embodiments thereof. For example, values for dark development potential ($V_{ddp}$) can range from about $-400$ to about $-975$. Preferred ranges for dark development potential for the imaging members of the present invention are usually about $-400$ to $-900$ volts with $-800$ volts being especially preferred in embodiments. High dark development potentials permit high contrast potentials, which result in images of high quality with essentially no background development.

The imaging members may also exhibit low dark decay values of, for example, about $-50$ volts per second or less. Low dark decay values can be of importance for developing high quality images since dark decay measures the amount of charge that disappears after charging of the photoreceptor, and a large difference in charge between exposed and unexposed areas of the photoreceptor results in images with high contrast. Acceptable values for dark decay vary depending on the design of the imaging apparatus in which the imaging members are contained. This dark decay may be as high as $-100$ volts per second with $-50$ volts, and $-10$ to $-20$ volts per second being preferred in embodiments.

Residual potential values ($V_R$) for the imaging members in embodiments thereof are excellent, ranging from, for example, about $-5$ volts to about $-50$ volts. Residual potential is a measure of the amount of charge remaining on the imaging member after erasure by exposure to light and prior to imaging. Residual potentials of $-5$ to $-15$ are considered very exceptional.

Photosensitivity values ($E_{0.5ddp}$ at 600 nanometers) for the imaging members in embodiments thereof are acceptable and, in some instances, excellent and can be, for example, from about 4 to about 25 ergs per square centimeter. Acceptable photosensitivity values vary depending on the design of the imaging apparatus in which the imaging members are contained; thus in some instances, values as high as 40 or 50 are acceptable, and values of about 5 can be preferred.

The present invention also encompasses a method of generating images with the photoconductive imaging members disclosed herein. The method comprises the steps of generating an electrostatic image on a photoconductive imaging member of the present invention, subsequently developing the electrostatic image with known developer compositions comprised of resin particles, pigment particles, additives, including charge control agents and carrier particles, reference U.S. Pat. Nos. 4,558,108; 4,560,535; 3,590,000; 4,264,672; 3,900,588 and 3,849,182, the disclosures of each of these patents being totally incorporated herein by reference, transferring the developed electrostatic image to a suitable substrate, and permanently affixing the transferred image to the substrate. Development of the image may be achieved by a number of methods, such as cascade, touchdown, powder cloud, magnetic brush, and the like. Transfer of the developed image to a substrate may be by any method, including those wherein a corotron or a biased roll is selected. The fixing step may be performed by means of any suitable method, such as flash fusing, heat fusing, pressure fusing, vapor fusing, and the like.

The imaging members can be prepared by a number of different known processes such as those illustrated in the U.S. Pat. No. 4,886,722, the disclosure of which is totally incorporated herein by reference. In one process embodiment, the azo photogenerator is coated onto a supporting substrate with a Bird applicator, for example, followed by the solution coating of the charge transport layer, and thereafter drying in, for example, an oven.

The following Examples are being supplied to further define various species of the present invention, it being noted that these examples are intended to illustrate and not limit the scope of the present invention. Parts and percentages are by weight unless otherwise indicated. Comparative Examples are also provided.

EXAMPLE I

Synthesis of phenyl 2-hydroxy-11H-benzo(a)carbazole-3-carboxylate 2-hydroxy-11H-benzo(a)carbazole-3-carboxylic acid (350 grams, 1.26 moles), phenol (480 grams, 5.1 moles) and 2 liters of xylene were charged in a 5 liter 3-necked flask equipped with a mechanical stirrer, a reflux condenser and a nitrogen inlet. The resulting mixture was stirred under a nitrogen atmosphere, followed by heating to reflux at an oil-bath temperature of about ($\sim$)160° C. Water was removed azeotropically by a Dean-Stark trap. Phosphorus oxychloride (262.5 grams) was then added through a pressure equalizing funnel slowly in $\sim$20 minutes. After the addition was completed, the mixture resulting was maintained at reflux for another 5 to 6 hours. TLC analysis revealed that all the starting acid was consumed. The product mixture was cooled to room temperature, and 1.5 liters of methanol was introduced therein. The resulting mixture was then chilled in an ice water bath for 1 hour, and the solid product was isolated by filtration. After washing with methanol (200 milliliters, twice) and vacuum drying, a yellow-green solid (369 grams) was obtained. The crude product was then dissolved in $\sim$ (about) 2 liters of hot acetone through a Soxhlet Extractor.

After cooling down the acetone solution to ice cold temperature, the yellow precipitate was isolated by filtration as a first crop. The filtrate was then concentrated to about 400 milliliters and about 100 milliliters of water was introduced. An additional amount of yellow precipitate was obtained (second crop) and was isolated by filtration. Both crop 1 and crop 2 were pure as determined by TLC analysis; the estimated purity was about 98 percent by NMR spectroscopy; total yield was 324.5 grams (73 percent).

m.p.: 273° to 275° C.

IR (KBr): 3,372 (N—H), 3,068 (aromatic C—H) and 1,689 cm$^{-1}$ (C=O).

MS (m/z): 353 (M+)

Analysis Calculated for: $C_{23}H_{15}NO_3$: C 78.17, H 4.28, N 3.96. Found: C 77.71, H 4.58, N 3.98.

EXAMPLE II

Synthesis of p-chlorophenyl 2-hydroxy-11H-benzo(a)carbazole-3-carboxylate:

2-Hydroxy-11H-benzo(a)carbazole-3-carboxylic acid (50 grams, 0.18 moles), p-chlorophenol (92 grams, 0.72 moles) and 250 milliliters of xylene were charged in a 500 milliliter 3-necked flask which was equipped with a magnetic stirrer, a reflux condenser and nitrogen inlet. The mixture was stirred under a nitrogen atmosphere and was heated to reflux at an oil bath temperature of $\sim$160° C. Phosphorus oxychloride (37.5 grams) was added through a pressure equalizing funnel slowly in $\sim$20 minutes. After the addition was completed, the mixture was maintained at reflux for another 4 hours. TLC analysis revealed that all the starting acid was consumed. The product mixture was cooled to room temperature, and 200 milliliters of methanol was introduced. The resulting mixture was chilled in an ice water bath for 1 hour, and the solid product was isolated by filtration. After washing with methanol (100 milliliters) and vacuum drying, a green solid crude product (60 grams) was obtained. The crude product was then dissolved in $\sim$200 milliliters of hot acetone through a Soxhlet Extractor. The purified product was isolated by adding water (200 milliliters) into the acetone solution; yield of yellow product solid was 53.4 (76 percent); estimated purity was 98 percent as determined by NMR spectroscopy.

m.p.: 304.5° to 305.5° C.

IR(KBr): 3,330 (N—H), 3,060 (aromatic C—H), 1,686 cm$^{-1}$ (C=O)

Analysis Calculated for: $C_{23}H_{14}NO_3Cl$: C 71.23, H 3.64, N 3.61. Found: C 71.05, H 3.94, N 3.64.

EXAMPLE III

Synthesis of 2-hydroxy-11H-benzo(a)carbazole-3-carboxanilide

The phenyl 2-hydroxy-11H-benzo(a)carbazole-3-carboxylate obtained from Example I (30 grams, 84 millimoles), aniline (33 grams, 336 millimoles) and 90 milliliters of N-methyl pyrrolidinone were charged into a 250 milliliter 3-necked flask equipped with a magnetic stirrer and a nitrogen inlet. The resulting mixture was stirred and was heated to reflux at an oil bath temperature of $\sim$250° C. under a nitrogen atmosphere. After 3 hours, TLC analysis revealed that all the starting phenyl ester was consumed. The mixture was cooled to room temperature and was poured into a 2 liter beaker containing 1 liter of ice cold 5 percent HCl. The yellow precipitate obtained was isolated by filtration. After washing with 100 milliliters of water and $\sim$20 milliliters of methanol and vacuum drying, 28.5 grams of crude product resulted. This product was then recrystallized from a mixture of DMF/MeOH/H$_2$O ($\sim$30 milliliters/$\sim$30 milliliters/$\sim$30 milliliters), yielding 22 grams (73 percent) of a yellow solid, which was subsequently identified as 2-hydroxy-11H-benzo(a)carbazole-3-carboxanilide.

m.p.: 334° to 336° C.

IR (KBr): 3,448 (O—H), 3,303 (N—H), 3,060 (aromatic C—H) and 1,657 cm$^{-1}$ (C=O). MS (m/z): 352 (M+)

Analysis Calculated for: $C_{23}H_{16}N_2O_2$: C 78.39, H 4.58, N 7.95. Found: C 78.14, H 4.54, N 7.91.

EXAMPLE IV

The phenyl 2-hydroxy-11H-benzo(a)carbazole-3-carboxylate obtained from Example I (5 grams, 14 millimoles), aniline (2.75 grams, 28 millimoles) and 15 milliliters of N-methyl pyrrolidinone were charged in a 100 milliliter 3-neck flask equipped with a magnetic stirrer and a nitrogen inlet. The resulting mixture was stirred and was heated to reflux at an oil bath temperature of $\sim$250° C. under a nitrogen atmosphere. After 3 hours, TLC analysis revealed that all the starting phenyl ester was consumed. The mixture was cooled to room temperature and was poured into a 1 liter beaker containing 400 milliliters of ice cold 5 percent of HCl. The yellow precipitate obtained was isolated by filtration. After washing with water (~200 milliliters) and ~20 milliliters of methanol and vacuum drying, 4.7 grams of crude product resulted. This product was then recrystallized from a mixture of (dimethylformamide) DMF/MeOH/$H_2O$ (~30 milliliter each) yielding 4.1 grams (83 percent) of 2-hydroxy-11H-benzo(a)carbazole-3-carboxanilide.

EXAMPLE V

The phenyl 2-hydroxy-11H-benzo(a)carbazole-3-carboxylate obtained from Example I (5 grams, 14 millimoles), aniline (27.5 grams, 280 millimoles) and 15 milliliters of N-methyl pyrrolidinone were charged in a 100 milliliter 3-neck flask equipped with a magnetic stirrer and a nitrogen inlet. The resulting mixture was stirred and was heated to reflux at an oil bath temperature of ~250° C. under a nitrogen atmosphere. After 3 hours, TLC analysis revealed that all the starting phenyl ester was consumed. The mixture was cooled to room temperature and was poured into a 1 liter beaker containing 400 milliliters of ice cold 5 percent HCl. The yellow precipitate obtained was isolated by filtration. After washing with water (~200 milliliters) and ~20 milliliters of methanol and vacuum drying, 5.0 grams of crude product resulted. This product was then recrystallized from a mixture of DMF/MeOH/$H_2O$ (~30 milliliter each) yielding 4.4 grams (88 percent) of 2-hydroxy-11H-benzo(a)carbazole-3-carboxanilide.

EXAMPLE VI

2-Hydroxy-11H-benzo(a)carbazole-3-carboxylic acid (0.5 gram, 1.8 millimoles) was reacted with aniline (0.44 gram, 4.5 millimoles) in 10 milliliters of o-dichlorobenzene in the presence of a condensing reagent, phosphorus oxychloride (0.37 gram, 2.4 millimoles), at reflux under a nitrogen atmosphere. After 5 hours, TLC analysis revealed that the starting acid was consumed, but that no anilide product, 2-hydroxy-11H-benzo(a)carbazole-3-carboxanilide, was formed.

Very similar results were obtained when 2-hydroxy-11H-benzo(a)carbazole-3-carboxylic acid was allowed to react in aniline (0.5 gram of acid in 10 milliliters of aniline) in the presence of an optional catalyst, such as $ZnCl_2$ or $ZnOAc_2$.

EXAMPLE VII

2-Hydroxy-11H-benzo(a)carbazole-3-carboxylic acid (40 grams, 0.144 millimoles), boron trifluoride methanol complex (71.3 milliliters, 0.429 millimoles) and 500 milliliters of methanol (stored over 3 Å molecular sieves) were charged in a 1 liter 3-necked flask which was equipped with a magnetic stirrer and a nitrogen inlet. The mixture was brought to reflux and the methanol condensate was continuously dried over molecular sieves using a Soxhlet extractor set-up. After ~28 hours, the product mixture was cooled to ice cold temperature, and excess boron trifluoride was destroyed by a sodium bicarbonate solution (~8 percent, 500 milliliters). The solid product was isolated by filtration and was washed by water and methanol (~100 milliliters each) to yield a crude product 18.6 grams after vacuum drying. TLC analysis revealed that the major component of the crude product was the desirable methyl ester product, the other detectable material was the starting material. The crude product was dissolved in ~170 milliliters of hot DMF, and insoluble impurities were removed by a filtration. To the hot filtrate, ~550 milliliters of acetic acid were added, and a yellow precipitated product resulted. The mixture of DMF/acetic acid solution was chilled in an ice bath to allow complete precipitation. A yellow product solid, which was identified as methyl 2-hydroxy-11H-benzo(a)carbazole-3-carboxylate, was isolated by filtration; yield was 14.1 grams (67 percent).

m.p.: 295° to 299° C.

IR (KBr): 3,368 (N—H), 3,060 (aromatic C—H), 2,948 (aliphatic C—H) and 1,675 $cm^{-1}$ (C=O).

MS (m/z): 291 (M+).

Methyl 2-hydroxy-11H-benzo(a)carbazole-3-carboxylate (4 grams, 13.7 millimoles) was allowed to react with neat aniline (20 milliliters) in a 200 milliliter 3-necked flask under a nitrogen atmosphore at reflux. After ~20 hours, TLC analysis suggested that all the methyl ester was consumed. The mixture was cooled to ice-cold temperature, and 200 milliliters of diethyl ether was added. The precipitated product was isolated by filtration yielding 1.13 grams of green solid. Pure anilide product can be obtained by extracting the crude product with ethyl acetate, (~100 milliliters) yielding 0.6 gram (12 percent) of anilide product.

EXAMPLE VIII

2-Hydroxy-11H-benzo(a)carbazole-3-carboxylic acid (1 gram, 3.6 millimoles) was stirred with an excess amount of thionyl chloride (1 gram, 8.4 millimoles) in ~10 milliliters of tetrahydrofuran. After 3 hours of stirring at room temperature, a dark brown solution of the acid chloride resulted. The excess thionyl chloride and the solvent tetrahydrofuran were removed under a reduced pressure. The resulting residue was redissolved in ~10 milliliters of fresh tetrahydrofuran; aniline (0.4 gram, 43 millimoles) and N,N-diethylaniline (0.6 gram, 41 millimoles) were then introduced to the tetrahydrofuran solution. The mixture was allowed to stir at room temperature overnight (16 hours). A small amount of yellow solid was observed. Solvent was removed on a rotary evaporator and the residue was digested with 20 milliliters of methylene chloride. A yellow green solid which was identified as 2-hydroxy-11H-benzo(a)carbazole-3-carboxanilide, was isolated by filtration with a low yield 0.65 gram (50 percent).

When the above procedure was scaled to a 5 gram level, the product isolated was impure. TLC analysis of the final product revealed that there are at least two minor unknown components in the product and these impurities could not be removed easily by recrystallization.

EXAMPLE IX

Other anilides of 2-hydroxy-11H-benzo(a)carbozole-3-carboxylic acid were prepared by repeating the procedures of Examples III, IV or V with the exceptions that there were selected as aniline reactants, p-chloroaniline, p-fluoroaniline, o-ethylaniline, o-methylaniline, p-methylaniline, m-trifluoromethylaniline, o-chloroaniline, o-fluoroaniline, and o-methoxyaniline, respectively. Synthetic data and physical properties of the resulting anilide products are summarized in FIG. 1, wherein compound product 15 is 2-hydroxy-11H-benzo(a)carbazole-3-carbox-p-chloroanilide, 16 is 2-hydroxy-11H-benzo(a)carbazole-3-carbox-p- fluoroanilide; 17 is 2-hydroxy-11H-benzo(a)carbazole-3-carbox-o-ethylaniline; 18 is 2-hydroxy-11H-benzo(a)carbazole-3-carbox-o-methylaniline; 19 is 2-hydroxy-11H-benzo(a)carbazole-3-carbox-p-methylaniline; 20 is 2-hydroxy-11H-benzo(a)carbazole-3-carbox-m-trifluoromethylanilide; 21 is 2-hydroxy-11H-benzo(a)carbazole-3-carbox-o-chloroanilide; 22 is 2-hydroxy-11H-benzo(a)carbazole-3-carbox-o-fluoroanilide; and 23 is 2-hydroxy-11H-benzo(a)carbazole-3-carbox-o-methoxyanilide.

EXAMPLE X

2-Hydroxy-8-chloro-11H-benzo(a)carbazole-3-carboxanilide was prepared by repreating the procedures in Examples III, IV, or V with the exception that phenyl 2-hydroxy-8-chloro-11H-benzo(a)carboxylate was selected in place of phenyl 2-hydroxy-11H-benzo(a)carboxylate; yield was 7.4 grams (74 percent).

m.p.: greater than 310° C.

IR(KBr): 3,300 and 3,438 (N—H), 3,040 (aromatic C—H) and 1,635 cm$^{-1}$ (amide C=O)

Analysis Calculated for: $C_{23}H_{15}N_2O_2Cl$: C 71.41, H 3.91, N 7.24. Found: C 71.71, H 3.92, N 7.35.

EXAMPLE XI

Other anilides of 2-hydroxy-8-chloro-11H-benzo(a)carbazole-3-carboxylic acid were prepared by repeating the procedures of Example X with the exceptions that there were selected as aniline reactants, m-fluoroaniline, o-chloroaniline, p-fluoroaniline, p-chloroaniline, o-ethylaniline, o-fluoroaniline, and m-trifluoromethylaniline, respectively. Synthetic data and physical properties of the resulting anilide products are summarized in FIG. 1 wherein compound product 24 is 2-hydroxy-8-chloro-11H-benzo(a)carbazole-3-carbox-m-fluoroanilide, 25 is 2-hydroxy-8-chloro-11H-benzo(a)carbazole-3-carbox-o-chloroanilide, 26 is 2-hydroxy-8-chloro-11H-benzo(a)carbazole-3-carbox-p-fluoroanilide, 27 is 2-hydroxy-8-chloro-11H-benzo(a)carbazole-3-carbox-p-chloroanilide, 28 is 2-hydroxy-8-chloro-11H-benzo(a)carbazole-3-carbox-o-ethylaniline, 29 is 2-hydroxy-8-chloro-11H-benzo(a)carbazole-3-carbox-o-fluoroanilide, and 30 is 2-hydroxy-8-chloro-11H-benzo(a)carbazole-3-carbox-m-trifluoromethylanilide.

EXAMPLE XII

2-Hydroxy-8-fluoro-11H-benzo(a)carbazole-3-carbox-p-chloroaniline was prepared by reacting phenyl 2-hydroxy-8-fluoro-11H-benzo(a)carbazole-3-carboxylate and p-chloroaniline using the procedure of Example X. Initially, 2-hydroxy-8-fluoro-11H-benzo(a)carbazole-3-carboxylic acid (2.96 grams, 0.01 mole), phenol (3.89 grams, 0.04 mole) and 10 milliliters of xylene were charged in a 100 milliliter 3-neck flask equipped with a magnetic stirrer, a reflux condenser and a nitrogen inlet. The resulting mixture was stirred under a nitrogen atmosphere, followed by heating to reflux at an oil bath temperature of ~160° C. Phosphorus oxychloride (1.75 grams) was then added through a pressure equalizing funnel slowly in ~10 minutes. After the addition was completed, the mixture was maintained at reflux for another two hours. TLC analysis revealed that all the starting acid was consumed. The product mixture was cooled to room temperature and ~10 milliliters of methanol were introduced therein. The resulting mixture was then chilled in an ice water bath for 1 hour, and the solid product was isolated by filtration. After washing with methanol (~10 milliliters) and vacuum drying, a yellow solid (2.64 grams) was obtained. The crude product was then dissolved in ~100 milliliters of hot acetone through a Soxhlet Extractor. After removal of the acetone on an evaporator, ~2.5 grams (70 percent) of purified phenyl 2-hydroxy-8-fluoro-11H-benzo(a)carbazole-3-carboxylate were obtained.

m.p.: 289° to 290° C.

IR(KBr): 3,364 (N—H) and 1,681 cm$^{-1}$ (amide C=O)

Analysis Calculated for: $C_{23}H_{14}NO_3F$: C 74.39, H 3.80, N 3.77. Found: C 73.50, H 4.13, N 3.76.

The phenyl 2-hydroxy-8-fluoro-11H-benzo(a)carbazole-3-carboxylate (2 grams, 5.4 millimoles), chloroaniline (4.13 grams, 32.4 millimoles) and 5 milliliters of N-methyl pyrrolidinone were charged into a 100 milliliter 3-neck flask which is equipped with a magnetic timer and a nitrogen inlet. The resulting mixture was stirred and was heated to reflux at an oil bath temperature of ~250° C. under a nitrogen atmosphere. After 4 hours, TLC analysis revealed that all the starting phenyl ester was consumed. The mixture was cooled to room temperature and poured into a 750 milliliter beaker containing 200 milliliters of 5 percent HCl. The yellow precipitate resulting was isolated by filtration. After washing with methanol (~10 milliliters) and ether (~10 milliliters), 1.8 grams of crude product were obtained. The crude product was then recrystallized from a mixture of DMF/MeOH/H$_2$O yielding 1.44 grams (66 percent) of a yellow solid, which was subsequently identified as 2-hydroxy-8-fluoro-11H-benzo(a)carbazole-3-carbox-p-chloroanilide.

m.p.: >310° C.

IR(KBr): 3,320 and 3,450 (N—H), 3,060 (aromatic C—H) and −1,681 cm$^{-1}$ (amide C=O)

Analysis Calculated for: $C_{23}H_{15}N_2O_2F$: C 68.24, H 3.48, N 6.92. Found: C 68.07, H 3.81, N 6.96.

EXAMPLE XIII

2-Nitro-4-aminophenyl-4'-aminophenylamine (1.22 grams, 5 millimoles) was stirred in an aqueous solution containing 30 milliliters of concentrated HCl and 10 milliliters of water at ~60° C. for 1 hour, and then overnight, about 16 hours, at room temperature. The yellow dispersion obtained was then cooled to about 0° to about 5° C. by an ice water bath. A cold aqueous solution of sodium nitrite (1 gram in 2.5 milliliters of water) was then added dropwise (in 15 minutes). After the addition, the resulting mixture was stirred in an ice bath for another 30 minutes. A clear dark brown solution resulted. This dark brown solution was filtered (by a medium sintered glass funnel) into a 250 milliliter precooled filtration flask. Hexafluorophosphoric acid (10 milliliters, 60 percent by weight) was then added into the aforementioned cold filtrate and a yellow precipitate was formed. The mixture resulting was stirred at ice cold temperature for another 30 minutes. The yellow precipitate resulting was collected by filtration. After washing with about 10 milliliters of cold water, about 10 milliliters of cold methanol and about 15 milliliters of ether, (about) ~2.7 grams of a tetrazonium hexafluorophosphate salt was obtained after air drying for about 20 minutes.

IR(KBr): 2,260 and 2,300 cm$^{-1}$ (—N+≡N).

The tetrazonium salt was dissolved in ~40 milliliters of cold DMF inside a 1 liter 3-neck flask which is surrounded by an ice water bath. A cold DMF solution containing 4.18 grams (11 millimoles) of the coupler synthesized in Example IX, 2-hydroxy-11H-benzo(a)- carbazole-3-carbox-o-ethylanilide in 250 milliliters of DMF was added into the salt solution in about 20 minutes. The color of the salt solution changed from orange to dark brown. A cold aqueous solution of 5 grams of NaOAc in 75 milliliters of water was added in 30 minutes. The temperature of the DMF solution was retained below 7° C. during the addition. After the addition was completed, the ice bath was removed and the product mixture was stirred at room temperature overnight, about 16 hours. Crude pigment product was isolated by filtration (fine sintered glass funnel). The crude product was then purified by washing with warm water (2×250 milliliters at 80° C.), warm DMF (3×250 milliliters at 80° C.), acetone, and ether, about 250 milliliters of each yielding a dark blue photogenerating pigment, 2-nitro-4,4'-(1''-azo-2''-hydroxy-11''H-benzo(a)carbazole-3''-carbox-o-ethylanilide)diphenylamine, 4.41 grams (84 percent).

m.p.: 288° C. (dec.)

IR(KBr): 1,675 cm$^{-1}$ (amide C=O)

Analysis Calculated for: $C_{63}H_{46}N_{10}O_6$: C 72.82, H 4.46, N 13.48. Found: C 71.59, H 4.56, N 13,40.

An imaging member was prepared with the above prepared azo photogenerating pigment. To a 1 ounce amber bottle there were added 52.8 milligrams of polyvinyl formal (obtained from Scientific Polymer Products, Inc., formal content 82 percent, acetate content 12 percent, hydroxy content 6 percent) and 10 milliliters of tetrahydrofuran. To the bottle was then added 211.1 grams of the bisazo pigment and about 90 grams of steel shot (⅛ inch diameter, number 302 stainless steel shot). The bottle was then placed on a Red Devil Paint Conditioner (Model 5100X) and shaken for about 30 minutes. The resulting dispersion was coated onto a 7.5 inch by 10 inch brush grained aluminum substrate obtained from Ron Ink Company using a Gardner Mechanical Drive with a 6 inch wide Bird Film Applicator (0.5 mil wet gap) inside a humidity-controlled glove box. The relative humidity of the glove box was controlled by dry air to about 25 percent, or less. The resulting charge generator layer was air dried for about 30 minutes and then vacuum dried for about 1 hour at 100° C. The thickness of the charge generator layer was estimated to be about 0.4 micron from TEM micrographs.

The above charge generator layer was overcoated with a charge transport layer prepared as follows. A solution containing 4.2 grams of MAKROLON®, a polycarbonate resin obtained from Larbensabricken Bayer A.G., 2.8 grams of N,N'-bis(3''-methylphenyl)-1,1'biphenyl-4,4'-diamine prepared as disclosed in U.S. Pat. No. 4,265,990, the disclosure of which is totally incorporated herein by reference, was prepared by dissolving the above materials in 31 milliliters of methylene chloride inside a 2 ounce amber bottle. The transport layer was obtained by coating the solution onto the charge generator layer using a 3.5 inch wide, 5 mil wet gap Bird Film Applicator, resulting in a transport layer about 27 microns thick. The resulting photoconductive device was air dried for about 1 hour and vacuum dried at 100° C. for about 16 hours before electrical testing.

The imaging member thus prepared was evaluated as follows. Xerographic measurements were made on a flat plate scanner using 2 inch by 2.5 inch samples of the imaging member prepared as described herein. The surface potential of the device was monitored with a capacitively coupled ring probe connected to a Keithley electrometer (Model 610C) in the coulomb mode. The output of the electrometer was displayed on a strip-chart recorder (HP Model 740A) which was calibrated by applying known voltage on an uncoated aluminum substrate. The exposure wavelength and the intensity were selected and adjusted using interference and neutral density filters, respectively. With the shutter closed, the dark decay was measured. With the shutter open, the photosensitivity at a known light exposure was recorded. The imaging member was charged to about −1,000 volts at the peak voltage and was allowed to discharge in the dark for 2 to 3 seconds to determine the dark decay. Subsequently, the imaging member was exposed to an erase lamp to photodischarge the surface charge and to determine its residual voltage ($V_R$). Thereafter, the imaging member was charged in a similar manner and exposed to visible radiation at the dark developer potential, and the sensitivity of the member was determined in terms of $E_į$, which represents the energy required to discharge half of the dark development potential. The imaging member exhibited a dark development potential ($V_{ddp}$) of −980 volts, a dark decay of −21 volts per second, an $E_{0.5ddp}$, the energy to discharge half the potential, at 450 nanometers (erg/cm$^2$) of 9.6, an $E_{0.5ddp}$, the energy to discharge half the potential, at 520 nanometers (erg/cm$^2$) of 7.4, an $E_{0.5ddp}$, the energy to discharge half the potential, at 600 nanometers (erg/cm$^2$) of 6.4, an $E_{0.5ddp}$, the energy to discharge half the potential, at 700 nanometers (erg/cm$^2$) of 7.1, an $E_{0.5ddp}$, the energy to discharge half the potential, at 750 nanometers (erg/cm$^2$) of 8.1, and an $E_{0.5ddp}$, the energy to discharge half the potential, at 790 nanometers (erg/cm$^2$) of 12.7.

EXAMPLE XIV 2,7-Diaminofluorenone, 1.05 grams, 5 millimoles, was stirred in 20 milliliters of 18 percent of hydrochloric acid at about 50° to about 60° C. for about one hour and then at room temperature, about 25° C., overnight, 18 hours. The yellow dispersion obtained was then cooled to about 0° to about 5° C. by an ice water bath. A cold aqueous solution of NaNO$_2$ (1 gram in 2.5 milliliters of water) was then added dropwise in about 15 minutes to the aforementioned yellow dispersion. After the addition of the NaNO$_2$ solution, the resulting mixture was stirred in an ice bath for 30 minutes. A clear dark brown solution resulted. This dark brown solution was filtered by a medium sintered glass funnel into a 250 milliliter precooled filtration flask. Fluoboric acid, 10 milliliters, was added to the cold filtrate and a yellow precipitate was formed immediately. This mixture of the filtrate and fluoboric acid was stirred at ice-cold temperature for about 30 minutes. The yellow precipitate was collected by filtration. After washing with cold water, cold methanol and ether, the product was air dried for 1 hour, yielding the tetrazonium salt, fluorenone-2,7-tetrazonium bis(tetrafluoroborate), about 1.85 grams.

The above prepared tetrazonium salt was then dissolved in about 40 milliliters of cold DMF solvent inside a 3-neck 1 liter flask surrounded by an ice water bath. A cold DMF solution containing 4.26 grams of the coupler, 2-hydroxy-11H-benzo(a)carbazole-3-carbox-p-chloroanilide, synthesized by the process of Example IX, in 250 milliliters of DMF was then added into the salt solution in about 20 minutes. The color of the salt solution changed from orange brown to dark purple. A cold solution of 5 grams of NaOAc in 75 millimeters of water was added slowly into the DMF solution (in 30 minutes). The temperature of the DMF solution was kept below 7° C. during the addition. After the addition was completed, the ice bath was removed and the product mixture was stirred at room temperature overnight. Crude bisazo pigment product was isolated by filtration (fine sintered glass funnel). The crude product was then transferred to a 750 milliliter beaker and was stirred with about 250 milliliters of water at about 81° C. for 2½ hours, overnight (18 hours) and then 2½ hours. After the third DMF wash, the pigment product was stirred in 250 milliliters of acetone and then 250 milliliters of ether (2½ hours each) to remove residual high boiling solvents of water and DMF, and the product was then dried inside a vacuum at 75° C. at 1.5 to 2.0 millimeters of mercury for 16 hours. A dark blue pigment product, 3.62 grams, about 72 percent yield, which was identified as 2,7-bis(1'-azo-2'-hydroxy-11'H-benzo(a)carbazole-3'-carbox-p-chloroanilide)fluorenone, was obtained.

m.p.: >350° C.

IR(KBr): 3,458 (N—H), 1,723 (C+O) and 1,678 cm$^{-1}$ (amide C=O).

Analysis calculated for: $C_{59}H_{34}N_8O_5Cl_2$: C 70.45, H 3.41, N 11.14. Found: C 69.27, H 3.41, N 10.46.

The above prepared pigment was further annealed for 16 hours in the vacuum oven at 135° C. at a reduced pressure of ~1.5 to 2.0 millimeters Hg. A weight loss of about 1.4 percent (water removal) was measured. An imaging member was then prepared with the aforementioned pigment by repeating the procedure of the aforementioned Example XIII with the following results. Maximum charge acceptance in volts was about −1,000; $V_{ddp}$ in volts was −900; dark decay in volts/second was −65; $E_{\frac{1}{2}}$ (ergs/cm$^2$) at 450 nanometers was 5.1; at 520 nanometers was 5.8; at 600 nanometers was 5.6; at 650 nanometers was 5.8; at 700 nanometers was 5.9; at 750 nanometers was 5.5; at 760 nanometers was 5.6 and at 800 nanometers was 9.1.

Other modifications of the present invention will occur to those of ordinary skill in the art subsequent to a review of the present application. These modification, and equivalents thereof are intended to be included within the scope of this invention.

What is claimed is:

1. A process which consists essentially of the reaction in an aromatic hydrocarbon solvent of 2-hydroxy-11H-benzo(a)carbazole-3-carboxylic acid, 2-hydroxy-8-chloro-11H-benzo(a)carbazole-3-carboxylic acid or 2-hydroxy-8-fluoro-11H-benzo(a)carbazole-3-carboxylic acid with a phenol, or substituted phenol, and a phosphorus oxychloride; isolating and purifying the resulting aromatic ester; and subsequently reacting the ester with an aniline in the presence of a polar solvent.

2. A process in accordance with claim 1 wherein the reaction with phenol is accomplished by heating.

3. A process in accordance with claim 1 wherein the reaction with phenol is accomplished by heating at a temperature of from about 80° to about 200° C.

4. A process in accordance with claim 1 wherein the aniline is chloroaniline, fluoroaniline, methylaniline, ethylaniline, methoxyaniline, trifluoromethylaniline, or nitroaniline.

5. A process in accordance with claim 1 wherein the reaction with phenol results in the formation of phenyl 2-hydroxy-11H-benzo(a)carbazole-3-carboxylate, phenyl 2-hydroxy-8-chloro-11H-benzo(a)carbazole-3-carboxylate, or 2-hydroxy-8-fluoro-11H-benzo(a)carbazole-3-carboxylate.

6. A process in accordance with claim 1 wherein the product is 2-hydroxy-11H-benzo(a)carbazole-3-carboxanilide.

7. A process in accordance with claim 1 wherein the product is 2-hydroxy-11H-benzo(a)carbazole-3-carbox-o-ethylanilide.

8. A process in accordance with claim 1 wherein the product is 2-hydroxy-11H-benzo(a)carbazole-3-carbox-p-chloroanilide.

9. A process in accordance with claim 1 wherein the anilide product is 2-hydroxy-1H-benzo(a)carbazole-3-carbox-p-methylanilide, 2-hydroxy-11H-benzo(a)carbazole-3-carbox-p-chloroanilide, 2-hydroxy-11H-benzo(a)carbazole-3-carbox-p-fluoroanilide; 2-hydroxy-11H-benzo(a)carbazole-3-carbox-o-ethylaniline; 2-hydroxy-11H-benzo(a)carbazole-3-carbox-o-methylaniline; 2-hydroxy-11H-benzo(a)carbazole-3-carbox-p-methylaniline; 2-hydroxy-11H-benzo(a)carbazole-3-carbox-m-trifluoromethylanilide; 2-hydroxy-11H-benzo(a)carbazole-3-carbox-o-chloroanilide; 2-hydroxy-11H-benzo(a)carbazole-3-carbox-o-fluoroanilide; 2-hydroxy-11H-benzo(a)carbazole-3-carbox-o-methoxyanilide, 2-hydroxy-8-chloro-11H-benzo(a)carbazole-3-carbox-m-fluoroanilide, 2-hydroxy-8-chloro-11H-benzo(a)carbazole-3-carbox-o-chloroanilide, 2-hydroxy-8-chloro-11H-benzo(a)carbazole-3-carbox-p-fluoroanilide, 2-hydroxy-8-chloro-11H-benzo(a)carbazole-3-carbox-p-chloroanilide, 2-hydroxy-8-chloro-11H-benzo(a)carbazole-3-carbox-o-ethylanilide, 2-hydroxy-8-chloro-11H-benzo(a)carbazole-3-carbox-o-fluoroanilide, 2-hydroxy-8-chloro-11H-benzo(a)carbazole-3-carbox-m-trifluoromethylanilide, or 2-hydroxy-8-fluoro-11H-benzo(a)carbazole-3-carbox-p-chloroanilide.

10. A process in accordance with claim 1 wherein the product has a purity of from about 95 to about 99 percent.

11. A process in accordance with claim 1 wherein the product is subjected to washing.

12. A process in accordance with claim 1 wherein the phenyl ester and the aniline are reacted in a solvent at a temperature of from about 140° C. to about 280° C.

13. A process in accordance with claim 12 wherein the solvent is dimethyl formamide, N,N-dimethylacetamide, or N-methyl pyrrolidinone.

14. A process in accordance with claim 1 wherein the aromatic hydroxy compound is phenol, chlorophenol, alkylphenol, alkoxyphenol, fluorophenol, nitrophenol or bromophenol.

15. A process in accordance with claim 1 wherein the ester is formed by heating at a temperature of from about 80° to about 200° C., and the anilide is formed by heating at a temperature of from about 140° to about 280° C.

16. A process in accordance with claim 1 wherein the ester is formed by heating at a temperature of from about 80° to about 200° C., and the anilide is formed by heating at a temperature of from about 140° to about 280° C.

17. A process in accordance with claim 1 wherein the solvent, acid, phenol or substituted phenol are admixed with the phosphorus oxyhalide.

18. A process in accordance with claim 1 wherein the aromatic hydrocarbon solvent is benzene or xylene, and the polar solvent is N-methyl pyrrolidone.

* * * * *